US011965152B2

(12) United States Patent
Webster et al.

(10) Patent No.: US 11,965,152 B2
(45) Date of Patent: Apr. 23, 2024

(54) BUFFER FORMULATION METHOD AND SYSTEM

(71) Applicant: Lonza Ltd., Visp (CH)

(72) Inventors: Thaddaeus Webster, Rollinsford, NH (US); Carrie Mason, Brentwood, NH (US); Tristan Wilkins, Newmarket, NH (US)

(73) Assignee: Lonza Ltd., Visp (CH)

( * ) Notice: Subject to any disclaimer, the term of this patent is extended or adjusted under 35 U.S.C. 154(b) by 1027 days.

(21) Appl. No.: 16/783,275

(22) Filed: Feb. 6, 2020

(65) Prior Publication Data

US 2020/0255792 A1 Aug. 13, 2020

Related U.S. Application Data

(60) Provisional application No. 62/803,747, filed on Feb. 11, 2019.

(51) Int. Cl.
*C12M 1/34* (2006.01)
*B01F 23/45* (2022.01)
(Continued)

(52) U.S. Cl.
CPC ............. *C12M 41/26* (2013.01); *B01F 23/45* (2022.01); *B01J 19/0086* (2013.01);
(Continued)

(58) Field of Classification Search
CPC .. C12M 41/48; C12M 1/3453; C12M 1/3407; C12M 41/12; C12M 29/26; C12M 41/00;
(Continued)

(56) References Cited

U.S. PATENT DOCUMENTS 4,101,275 A * 7/1978 Taguchi ................. G01N 35/00
436/103
4,245,509 A * 1/1981 Mody ................ G01N 35/1097
73/863.86
(Continued)

FOREIGN PATENT DOCUMENTS

JP 2008203129 9/2008
JP 2015117883 6/2015
(Continued)

OTHER PUBLICATIONS

PCT/US2020/016937 International Search Report and Written Opinion dated Jun. 24, 2020.

*Primary Examiner* — Shogo Sasaki
(74) *Attorney, Agent, or Firm* — Dority & Manning, P.A.

(57) ABSTRACT

The monitoring and control of bioprocesses is provided. More particularly, the present disclosure is directed to formulating buffer products from multiple buffer solutions for feeding the different operations occurring within a bioprocess line. As the buffer product is being formulated, the buffer product is tested for conductivity, refractive index, and optionally pH. The conductivity measurements are used in conjunction with refractive index measurements to ensure that the buffer product not only has the correct concentration of ions but also has the correct concentration of components. A controller can be used to make automatic adjustments to the buffer product should any of the measured parameters fall outside a preset range.

21 Claims, 2 Drawing Sheets

(51) Int. Cl.
*B01J 19/00* (2006.01)
*B01F 101/22* (2022.01)

(52) U.S. Cl.
CPC ........ *C12M 1/3407* (2013.01); *C12M 1/3453* (2013.01); *C12M 41/12* (2013.01); *B01F 2101/22* (2022.01); *Y10T 436/108331* (2015.01)

(58) Field of Classification Search
CPC ........ C12M 41/26; C12M 41/32; B01F 23/45; B01F 2101/22; B01J 19/0086; Y10T 436/108331
See application file for complete search history.

(56) References Cited

U.S. PATENT DOCUMENTS

| | | | | |
|---|---|---|---|---|
| 4,253,847 A * | 3/1981 | Matson | ............ | G01N 33/48714 436/83 |
| 4,441,374 A * | 4/1984 | Suzuki | ............ | G01N 1/38 73/864.22 |
| 4,794,806 A * | 1/1989 | Nicoli | ............ | G05D 11/132 250/576 |
| 4,836,038 A * | 6/1989 | Baldwyn | ............ | G01N 30/24 73/864.21 |
| 5,007,297 A * | 4/1991 | Sommer | ............ | G01N 15/10 73/865.5 |
| 5,077,017 A * | 12/1991 | Gorin | ............ | G01N 1/38 422/514 |
| 5,080,866 A * | 1/1992 | Petty | ............ | G01N 35/085 436/51 |
| 5,221,521 A * | 6/1993 | Hashizume | ............ | G01N 1/38 422/514 |
| 5,656,491 A | 8/1997 | Cassani et al. | | |
| 5,783,450 A * | 7/1998 | Yoshida | ............ | G01N 30/88 436/172 |
| 5,928,953 A * | 7/1999 | Kallback | ............ | G01N 35/1097 422/68.1 |
| 6,211,956 B1 * | 4/2001 | Nicoli | ............ | G01N 15/02 356/337 |
| 6,324,924 B1 * | 12/2001 | Peterson | ............ | G01N 35/1097 73/863 |
| 7,629,167 B2 | 12/2009 | Hodge et al. | | |
| 8,298,054 B2 | 10/2012 | Hodge et al. | | |
| 10,421,939 B2 | 9/2019 | Ray et al. | | |
| 2002/0011437 A1 * | 1/2002 | Kaito | ............ | G01N 30/34 210/198.1 |
| 2004/0259262 A1 * | 12/2004 | Ishii | ............ | G01N 21/643 436/172 |
| 2006/0104827 A1 * | 5/2006 | Shaw | ............ | G01N 35/1097 417/244 |
| 2006/0127237 A1 * | 6/2006 | Shaw | ............ | G01N 1/38 417/313 |
| 2008/0292534 A1 * | 11/2008 | Richardson | ............ | C01B 11/022 422/236 |
| 2009/0104594 A1 | 4/2009 | Webb | | |
| 2009/0305626 A1 | 12/2009 | Hope | | |
| 2011/0280797 A1 | 11/2011 | Mohtadi et al. | | |
| 2012/0077429 A1 | 3/2012 | Wernimont et al. | | |
| 2013/0280797 A1 | 10/2013 | Rao et al. | | |
| 2014/0166555 A1 | 6/2014 | Dibel | | |
| 2016/0097074 A1 | 4/2016 | Collins et al. | | |
| 2016/0243512 A1 | 8/2016 | Brandt | | |
| 2017/0253848 A1 | 9/2017 | Emmerson et al. | | |
| 2018/0037861 A1 | 2/2018 | Wilkins | | |

FOREIGN PATENT DOCUMENTS

WO    WO 2006/071716    7/2006
WO    WO 2015/117883    8/2015

\* cited by examiner

BUFFER FORMULATION METHOD AND SYSTEM

RELATED APPLICATIONS

The present application is based on and claims priority to U.S. Provisional Patent application Ser. No. 62/803,747, filed on Feb. 11, 2019, which is incorporated herein by reference.

BACKGROUND

Bioreactors, which are apparatuses in which biological reactions or processes can be carried out on a laboratory or industrial scale, are used widely within the biopharmaceutical industry. Bioreactors can be used to produce all different types of bioproducts. Bioproducts can include, for instance, cell cultures and materials derived from cell cultures including beverages, biofuels, bioenergy, biochemicals, antibiotics, amino acids, enzymes, monoclonal antibodies, monomers, proteins, food cultures, biopolymers, alcohols, flavorings, fragrances, and the like. In some embodiments, cell cultures can be grown for cell therapy. Cell therapy is the prevention, treatment, cure or mitigation of disease or injuries in humans by the administration of autologous, allogeneic or xenogeneic cells that have been manipulated or altered ex vivo. One goal of cell therapy is to repair, replace or restore damaged tissues or organs.

Cell cultures are typically grown in batch processes where the biological material remains in the bioreactor until the end of the reaction time. In certain of these processes, fluid medium contained within the bioreactor can be periodically or continuously removed and resupplied in order to replenish nutrients contained within the fluid medium and for possibly removing damaging by-products that are produced during the process.

During the growth of cell cultures, various fluids are formulated and fed to different parts of the process. Such fluids can include nutrient mediums, various different types of reagents, and buffer formulations. Buffer formulations, for instance, are not only used to maintain a desired pH level within cell cultures but are also used in many downstream processes during purification of the end product. For example, buffer formulations are used during chromatography and/or during various different filtering operations. The buffer formulation needed for one unit operation process, however, can be very different from the buffer formulation needed for other processes.

In the past, large quantities of the different buffer formulations were stored in large tanks and fed to the bioprocess when needed. Maintaining individual buffer formulations in large quantities, however, can be inefficient, can require significant amounts of space, and can provide little to no flexibility. Further, as the complexity of bioprocesses increases, the number of different buffer formulations continues to increase thereby exacerbating the above problems.

In view of the above, a need exists for an inline buffer formulation system capable of formulating buffer solutions continuously and inline. One problem with formulating buffer solutions inline, however, is the ability to maintain quality control of the different solutions in order to ensure that the buffer formulations contain the desired amount of buffer components in the desired concentrations. Thus, a need exists not only for an inline system for producing buffer formulations but also for a monitoring and control system for ensuring that the buffer products are correctly formulated.

SUMMARY

In general, the present disclosure is directed to an inline buffer formulation system and method that is capable of mixing multiple buffer solutions to produce final buffer products for downstream processes. In accordance with the present disclosure, the buffer products can be monitored in order to ensure that the buffer components contained within the final buffer products are maintained within preset limits in order to confirm that the final buffer products meet desired buffer specifications for the different downstream process requirements. In one embodiment, for instance, an orthogonal method is utilized that monitors changes in the final buffer product being formulated from multiple buffer solutions.

In one embodiment, for instance, the present disclosure is directed to a process for formulating buffer products for feeding to a bioprocess. The process includes the steps of combining multiple buffer solutions to form a final buffer product. The multiple buffer solutions can include at least a first buffer solution and a second buffer solution. In various embodiments, the process can include a third buffer solution, a fourth buffer solution, a fifth buffer solution, etc. A conductivity, a pH and/or a temperature of the final buffer product are measured after the final buffer product has been formulated. In addition, a refractive index is measured for the final buffer product. The measured conductivity is then compared to a preset conductivity range. In addition, the measured refractive index is compared to a preset refractive index range. The flow rate of at least one of the buffer solutions in relation to the other buffer solutions is then selectively adjusted in order to maintain the conductivity and the refractive index of the buffer product within the preset ranges. In one embodiment, the final buffer product is formed inline and the process is continuous. In addition, the conductivity and refractive index of the final buffer product can be continuously monitored as the buffer product is being formulated. A controller, such as one or more microprocessors, can be utilized and configured to receive the conductivity and refractive index data and can automatically control the flow rates of the buffer solutions based upon the measured parameters. The conductivity of the final buffer product and the refractive index of the final buffer product can have a preset limit. The preset refractive index range can be within about 10% of the preset refractive index limit. Similarly, the preset conductivity range can be within about 10% of the preset conductivity limit. In one embodiment, the refractive index of each buffer solution can also be measured as each buffer solution is being combined to form the final buffer product. The measured refractive index of each buffer solution can also be fed to the controller for use in determining the respective flow rates.

Each of the buffer solutions can contain various different buffer components. For example, at least one of the buffer solutions can contain a concentrated buffer component that becomes diluted in the final buffer product. Buffer components that may be contained in the buffer solutions include tricine, bicine, a sulfonic acid, sodium cacodylate, sodium acetate, sodium phosphate, sodium chloride, an acetic acid, glycinamide, or acetamidoglycine. In one embodiment, the first buffer solution and the second buffer solution include at least one common cation or anion.

The final buffer product can be changed inline and fed to various downstream processes. For instance, the buffer product can be fed to a cell culture containing, for instance, mammalian cells. In other embodiments, the final buffer product can be fed to a chromatography process and/or to a filtration process.

The present disclosure is also directed to a system for formulating buffer products. In one embodiment, the system includes a bioreactor defining a hollow interior for receiving a cell culture. The bioreactor can include a plurality of ports for feeding and/or removing materials from the hollow interior. A nutrient media feed can be included for feeding a nutrient media to the hollow interior of the bioreactor. The nutrient media feed can be in fluid communication with at least one of the ports on the bioreactor. The system can further include a buffer product feed that can be in communication with one of the ports on the bioreactor and/or in communication with various downstream processes that process the cells and/or a bioproduct collected from the cells contained in the bioreactor. The buffer product feed is in communication with a plurality of buffer solution feeds. The buffer solution feeds are configured to hold buffer solutions that are then combined together in controlled ratios in order to formulate a buffer product.

In accordance with the present disclosure, the system further includes a temperature sensor for measuring the temperature of the buffer product as it is being formed, a conductivity probe for measuring the conductivity of the buffer product as it is being formed, a pH sensor for measuring pH, and a refractive index measuring device for measuring the refractive index of the buffer product as it is being formed. The temperature sensor, pH sensor, conductivity probe, and refractive index measuring device can be in communication with a controller that receives temperature measurements, pH measurements, conductivity measurements, and refractive index measurements. The controller, based upon at least certain of the conductivity measurements and/or refractive index measurements is configured to selectively increase or decrease flow of one or more buffer solutions for maintaining the buffer product within preset limits. For example, each of the buffer solution feeds can include a flow control device for controlling flow of a buffer solution from each buffer solution feed. The controller can be configured to control each of the flow control devices for selectively adjusting flow rates.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to a process and system for producing different buffer products. The buffer products can be formed inline and fed to various operations occurring within a bioprocess. The bioprocess, for example, can include a bioreactor for propagating a cell culture in order to produce a bioproduct, such as an enzyme, a protein, or the like. The bioprocess may further include purification systems, such as downstream chromatography and/or filtration. In accordance with the present disclosure, buffer formulations can be formed inline from multiple buffer solutions and fed to the various different subprocesses that occur within the bioprocess. The buffer products formulated, for instance, can be fed to the bioreactor, to a chromatography operation, and/or to a filtration operation. In accordance with the present disclosure, various controls can be incorporated into the buffer formulation system to ensure that the buffer products contain the desired components in the desired concentrations prior to being fed to a subprocess within the bioprocess.

For example, in one embodiment, an orthoganol method is utilized that monitors changes in buffer products being formulated from multiple buffer solutions. For example, the conductivity, the refractive index, and/or the pH of the buffer product can be continuously monitored. A controller, such as a microprocessor, can be configured to confirm that the buffer product meets target specifications. In one embodiment, the controller can be configured to make changes to the buffer product by controlling different buffer solution feeds to ensure that the buffer product stays within specifications.

As a buffer product is produced from multiple buffer solutions, in one embodiment, the buffer product can be continuously monitored for conductivity and refractive index. Both of these measurements measure different characteristics of the buffer product fluid. In accordance with the present disclosure, both measurements are used in combination in order to ensure that the buffer product is within specifications.

Conductivity measurements, for instance, measure the ability of the solution to transfer electric current. Conductivity, for instance, indicates the amount or concentration of dissolved solutes within the buffer product. Although measuring the conductivity of the buffer product allows for a relatively accurate assessment of the concentration of electrically conductive ions in the solution, conductivity measurements do have some drawbacks. In particular, conductivity measurements are limited by the ability to measure concentrations of solution containing nonionic and weakly ionic substances.

Another drawback that can occur with conductivity measurements is the ability to discern differences between solutes that may have a common anion or cation. For example, conductivity measurements of a solution containing multiple solutes having the same anion or cation, e.g. a solution containing both sodium phosphate and sodium chloride, does not provide enough information to determine whether each of the solutes are in the solution in the correct proportioned amounts.

In this regard, the conductivity of the buffer product is measured in conjunction with measuring the refractive index. A refractive index measurement is a measurement of the speed of light in a medium. The index of refraction in a liquid changes as the concentration of a solute changes. Thus, solutions with different concentrations of a given solute will have different refractive indices. Unlike conductivity, refractive index measurements are not strength of ion dependent.

Thus, conductivity and refractive index measurements can provide relatively instantaneous information about a solution albeit in a different manner. In accordance with the present disclosure, both conductivity measurements and refractive index measurements are taken of the buffer product in order to ensure that the buffer product is made with the proper components and the correct concentrations. Through the use of both measurement techniques, the present disclosure uses an orthoganol monitoring system for maintaining buffer products within preset concentration ranges.

Monitoring both the conductivity and the refractive index of buffer products made by the buffer formulation system can provide various advantages and benefits. For instance, conductivity measurements alone or refractive index measurements alone do not provide sufficient information and detail regarding the concentration of the various components contained within the buffer product. By monitoring both conductivity and refractive index and by comparing each of these measurements in combination, the amount of estimating or guess work needed to determine if the concentration of the components in the buffer product are minimized. Using both refractive index measurements and conductivity measurements, for instance, helps identify and actually fingerprint individual buffer products, which can be very valuable when creating buffer products inline and in real time.

Figure 1:
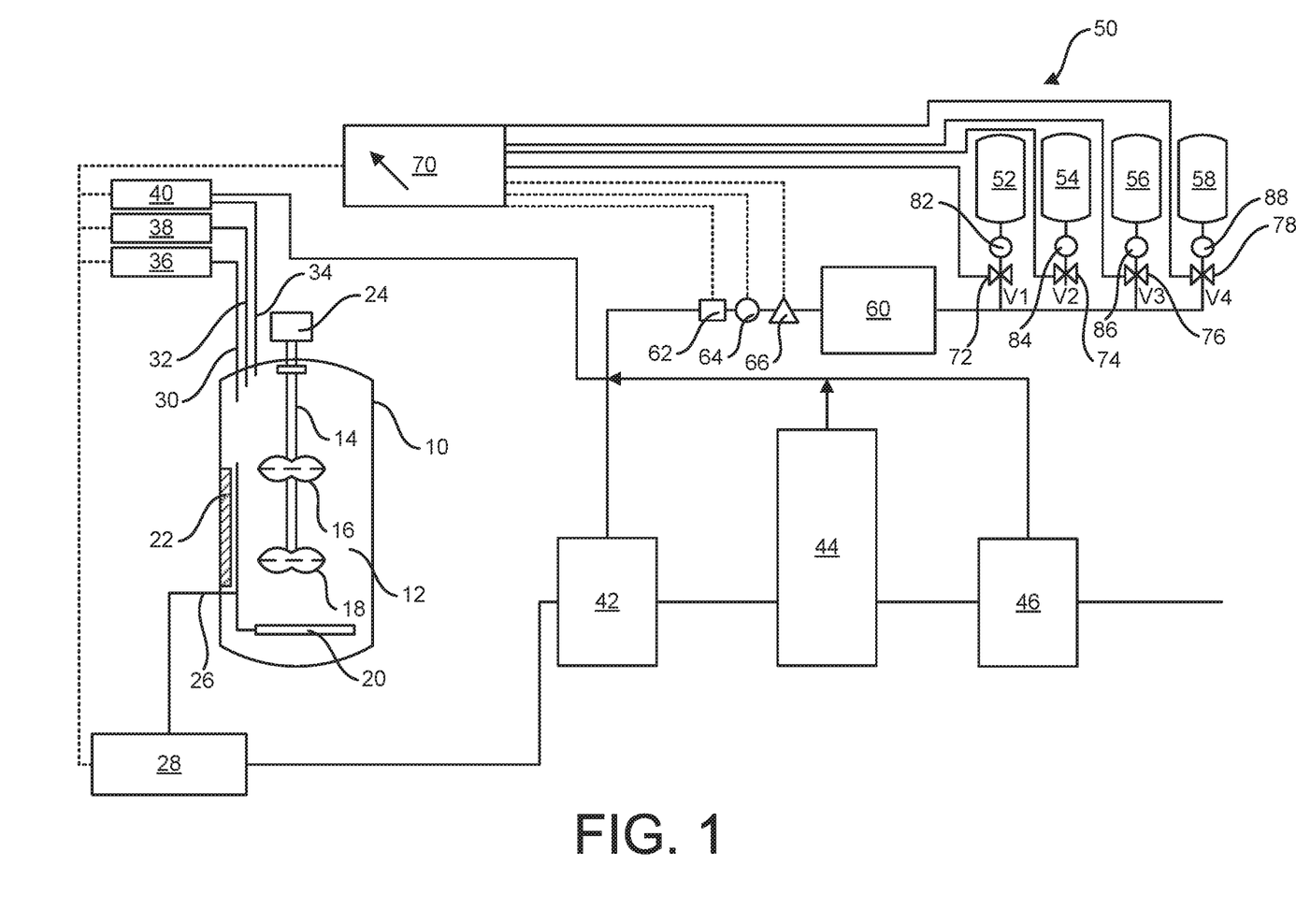
FIG. 1 is a schematic diagram of one embodiment of a bioreactor system made in accordance with the present disclosure.

In one embodiment, the system and process for producing buffer products occurs within a bioprocess during the harvesting of a cell culture. Buffer products made according to the present disclosure can be fed directly to a bioreactor, but also are used in many downstream processes. For exemplary purposes only, FIG. 1 illustrates one example of a bioprocess that may incorporate the system and process for producing buffer products in accordance with the present disclosure. The bioreactor system includes a bioreactor 10. In general, the system and process of the present disclosure can use any suitable bioreactor. The bioreactor, for instance, may comprise a fermenter, a stirred-tank reactor, an adherent bioreactor, a wave-type bioreactor, a disposable bioreactor, and the like. In the embodiment illustrated in FIG. 1, the bioreactor 10 comprises a hollow vessel or container that includes a bioreactor volume 12 for receiving a cell culture within a fluid growth medium. As shown in FIG. 1, the bioreactor system can further include a rotatable shaft 14 coupled to an agitator such as dual impellers 16 and 18 and to a motor 24.

The bioreactor 10 can be made from various different materials. In one embodiment, for instance, the bioreactor 10 can be made from metal, such as stainless steel. Alternatively, the bioreactor 10 may comprise a single use bioreactor made from a rigid polymer or a flexible polymer film.

The bioreactor 10 can have any suitable volume. For instance, the volume of the bioreactor 10 can be from 0.1 mL to about 25,000 L or larger. For example, the volume 12 of the bioreactor 10 can be greater than about 0.5 L, such as greater than about 1 L, such as greater than about 5 L, such as greater than about 10 L. The volume of the bioreactor 10 is generally less than about 25,000 L, such as less than about 15,000 L, such as less than about 10,000 L, such as less than about 5,000 L, such as less than about 1,000 L, such as less than about 100 L, such as less than about 50 L, such as less than about 20 L.

In addition to the impellers 16 and 18, the bioreactor 10 can include various additional equipment, such as baffles, spargers, gas supplies, heat exchangers or thermal circulator ports, and the like which allow for the cultivation and propagation of biological cells. For example, in the embodiment illustrated in FIG. 1, the bioreactor 10 includes a sparger 20 and a baffle 22.

As shown in FIG. 1, the bioreactor 10 also includes a plurality of ports. The ports can allow supply lines and feed lines into and out of the bioreactor 10 for adding and removing fluids and other materials. In addition, the one or more ports may be for connecting to one or more probes for monitoring conditions within the bioreactor 10. In addition, the bioreactor 10 and be placed in association with a load cell for measuring the mass of the culture within the bioreactor.

In the embodiment illustrated in FIG. 1, the bioreactor 10 includes a bottom port 26 connected to an effluent 28 for withdrawing materials from the bioreactor continuously or periodically. Materials can be withdrawn from the bioreactor 10 using any suitable method. For instance, in an alternative embodiment, an effluent can be removed from the bioreactor 10 from the top of the bioreactor using a dip tube. In addition, the bioreactor 10 includes a plurality of top ports, such as ports 30, 32, and 34. Port 30 is in fluid communication with a first fluid feed 36, port 32 is in fluid communication with a second feed 38 and port 34 is in fluid communication with a third feed 40. The feeds 36, 38 and 40 are for feeding various different materials to the bioreactor 10, such as a nutrient media.

As shown in FIG. 1, the bioreactor can be in communication with multiple nutrient feeds. In this manner, a nutrient media can be fed to the bioreactor containing only a single nutrient for better controlling the concentration of the nutrient in the bioreactor during the process. In addition or alternatively, the different feed lines can be used to feed gases and liquids separately to the bioreactor.

Once a cell culture has been propagated in the bioreactor 10, in one embodiment, the cell culture is fed to a harvest system for harvesting a bioproduct. Not shown, for instance, the system may include a harvest tank, and a centrifuge. In many systems, the bioproduct being harvested can then be fed to downstream purification processes. For example, in FIG. 1, the bioproduct harvested from the bioreactor 10 can be fed to a first filtration device 42, a chromatography device 44, and a second filtration device 46. It should be understood that the system illustrated in FIG. 1 is merely exemplary and the system can include more than one chromatography device, less than two filtration devices or more than two filtration devices as desired.

The filtration devices 42 and 46 may include a variety of filtration mechanisms. For example, in one embodiment, one of the filtration devices may comprise a tangential flow filtration (TFF) device. A tangential flow filtration device, for instance, may enable the diafiltration of the product stream. A tangential flow filtration device may include two stages; volume reduction and diafiltration. During the volume reduction step, the bulk volume of the cell culture medias is filtered out through the permeate side of the filter until a desired product concentration is reached in the holding tank. In a diafiltration stage following the volume reduction stage, the concentrated product is washed with a fluid, such as a buffer, to remove cell culture or harvest media components that are undesired or are unacceptable. Further volume reduction may also be carried out after diafiltration to reach a desired product density.

In one embodiment, the filtration devices 42 and 46 may use ultrafiltration. During ultrafiltration, the product stream is fed through a semipermeable membrane. Suspended solids and solutes of high molecular weight are retained as a retentate, while water and low molecular weight solutes pass through the membrane as the permeate. Ultrafiltration is particularly well suited to purifying and concentrating protein solutions. In one embodiment, ultrafiltration can be used with diafiltration as described above. The chromatography device 44 as shown in FIG. 1 may use various different chromatography methods such as affinity chromatography, gel filtration chromatography, ion exchange chromatography, reversed phase chromatography, hydrophobic interaction chromatography, and the like.

The process and system of the present disclosure, for instance, can use any suitable chromatography method.

Similar to the filtration devices 42 and 46, the chromatography device 44 also needs a buffer for proper operation of the device. The buffer needed for the chromatography device 44 can be different than the buffer needed for the first filtration device 42 which can also be different than the buffer needed for the second filtration device 46. Also, as described above, the system can include more filtration devices and more chromatography devices leading to the necessity for even a greater number of different buffers.

In this regard, the system as shown in FIG. 1 includes a buffer distribution subsystem 50. The buffer distribution subsystem 50 is shown in greater detail in FIG. 2. The buffer distribution subsystem 50 includes a plurality of buffer feed tanks that each contain a different buffer solution. The different buffer solutions are used to formulate a buffer product for feeding to the bioprocess. In the embodiment illustrated in the figures, for instance, the system includes buffer feed tanks 52, 54, 56 and 58. In general, the system can include anywhere from 2 to about 12 buffer feed tanks. The embodiment illustrated in the figures is for exemplary purposes only. The buffer feed tanks 52, 54, 56 and 58 are in fluid communication with a mixing device 60 for formulating a buffer product from the different buffer solutions. The mixing device 60 can comprise any suitable mixing apparatus. For example, the mixing device 60 may be a mixing tank. In an alternative embodiment, the mixing device 60 may be an inline mixing device.

In accordance with the present disclosure, once a buffer product is formulated from the buffer solutions, the final buffer product is monitored to ensure that the buffer product is within specifications and contains the correct components in the correct proportionate amounts. In this regard, the buffer product is in fluid communication with various different measuring devices. In the embodiment illustrated in the figures, for instance, the system includes a conductivity probe 62, a refractive index measuring device 64, and a pH probe 66. In addition, the system can include a temperature measurement device. Refractive index measurements and conductivity measurements, for instance, can be temperature dependent. In this regard, temperature measuring device may be incorporated into the conductivity probe 62 and/or the refractive index measuring device 64.

As shown in FIG. 1, the system can further include a controller 70. The controller may comprise one or more programmable devices or microprocessors. As shown, the controller 70 can be in communication with the one or more feeds 36, 38 and 40 and with one or more effluents 28. In addition, the controller 70 can control the buffer distribution subsystem 50. For instance, the controller 70 is configured to receive measurements and other data from the conductivity probe 62, the refractive index measuring device 64, and the pH probe 66. In addition, the controller 70 can control the flow of a buffer solution from each of the buffer feed tanks 52, 54, 56 and 58. For instance, buffer feed tank 52 includes a flow control device 72, buffer feed tank 54 includes a flow control device 74, buffer feed tank 56 includes a flow control device 76 and buffer feed tank 58 includes a flow control device 78. The flow control devices 72, 74, 76 and 78 control the amount of each respective buffer solution that is used to produce the buffer product within the mixing device 60. In addition, each flow control device 72, 74, 76 and 78 is in communication and controlled by the controller 70. In this manner, the controller 70 can be used to formulate a buffer product in the mixing device 60, monitor the buffer product being formed, and make corrections or changes as desired.

For example, once a buffer product is formulated, conductivity measurements, refractive index measurements, and the pH of the buffer product can be fed to the controller 70. The controller 70 can compare the measured parameters to a predetermined or preset limit or predetermined range for each parameter.

For example, the controller 70 can receive conductivity measurements from the conductivity probe 62 and compare the measured conductivity to a preset conductivity range. If the measured conductivity is outside of the preset range, the controller 70 can be configured to alter the flow rate of the buffer solutions by controlling the flow control devices 72, 74, 76 and 78 in order to take corrective action to ensure that the buffer product stays within the preset conductivity range. Similarly, the controller 70 can receive refractive index measurements and compare them to a preset refractive index range. If the buffer product is outside of the preset refractive index range, the controller 70 can control flow of the buffer solutions and change the relative proportions of the buffer solutions in order to maintain the buffer product within the preset refractive index range. The controller 70 can also take the same corrective action with respect to pH and any other measurements made on the buffer product. In formulating the buffer product, the controller 70 can be programmed with the particular buffer solutions contained in each of the buffer solution tanks 52, 54, 56 and 58 and can be preprogrammed with a recipe for creating the desired buffer product that is to be fed to one location within the bioprocess. For instance, as shown in FIG. 1, the particular bioproduct formulated can be fed alternatively to the bioreactor 10 through the feed port 40, to the first filter device 42, to the chromatography device 44, or to the second filter device 46.

The present conductivity range and the preset refractive index range can be set and determined based upon various different factors. In one embodiment, a buffer product made according to a certain recipe has a conductivity set point and a refractive index set point as determined according to a particular temperature. The controller 70 can be programmed with a preset conductivity range and/or a preset refractive index range that is within tolerance limits of the conductivity set point and refractive index set point. For instance, in one embodiment, the preset conductivity range can be within about 15%, such as within about 10%, such as within about 5% of the conductivity set point. Similarly, the refractive index range can be within about 15%, such as within about 10%, such as within about 5% of the refractive index set point.

The buffer solutions contained in the buffer solution feed tanks 52, 54, 56 and 58 can vary depending upon the particular application. In one embodiment, for instance, at least one of the buffer solutions contains a bicarbonate solution for maintaining a given pH level within a target environment, such as within a bioreactor. Other buffer solutions that may be contained in the buffer solution tanks include at least one of tricine, bicine, a sulfonic acid, sodium cacodylate, sodium acetate, sodium phosphate, sodium chloride, an acetic acid, glycinamide, acetamidoglycine, or mixtures thereof.

Various buffer components that may be contained in the buffer solution can include any of the following: tris(hydroxymethyl) aminomethane, tricine, 4-(2-hydroxyethyl)-1-piperazive ethane sulfonic acid, 3-(N-morpholino)propane sulfonic acid, piperazine-N-n'-bis(2-ethanesulfonic acid), [tris(hydroxymethyl)methylamino] propanesulfonic acid, bicine, N,N-bis[2-hydroxyethyl]-2-aminoethanesulfonic acid, 2-[[1,3-dihydroxy-2-(hydroxymethyl)propan-2-yl] amino]ethanesulfonicacid, sodium cacodylate, 2-(N-morpholino) ethanesulfonic acid, acetate, 2[(2-amino-2-oxoethyl)-(carboxymethyl) amino] acetic acid, N-(2-acetamido)-2-aminoethanesulfonic acid, glycinamide, acetamidoglycine, acetic acid, or mixtures thereof.

In addition to varying the different buffer components contained in each of the buffer solutions, the concentration of each component can also vary. In one embodiment, for instance, the buffer components can be contained in the buffer solutions at relatively high concentrations that are later diluted when producing buffer products. For instance, in one embodiment, a diluent, such as distilled water, can also be placed in communication with the mixing device 60 for formulating the buffer product.

Many of the buffer components contained within the buffer solutions have a common anion or cation. Thus, many buffer products will contain buffer components with the same cation or anion. By using a conductivity probe in conjunction with a refractive index measurement device, however, both measurements can be used to ascertain whether the correct buffer component is present and whether the buffer component is present in the buffer product at the desired concentration levels.

Figure 2:
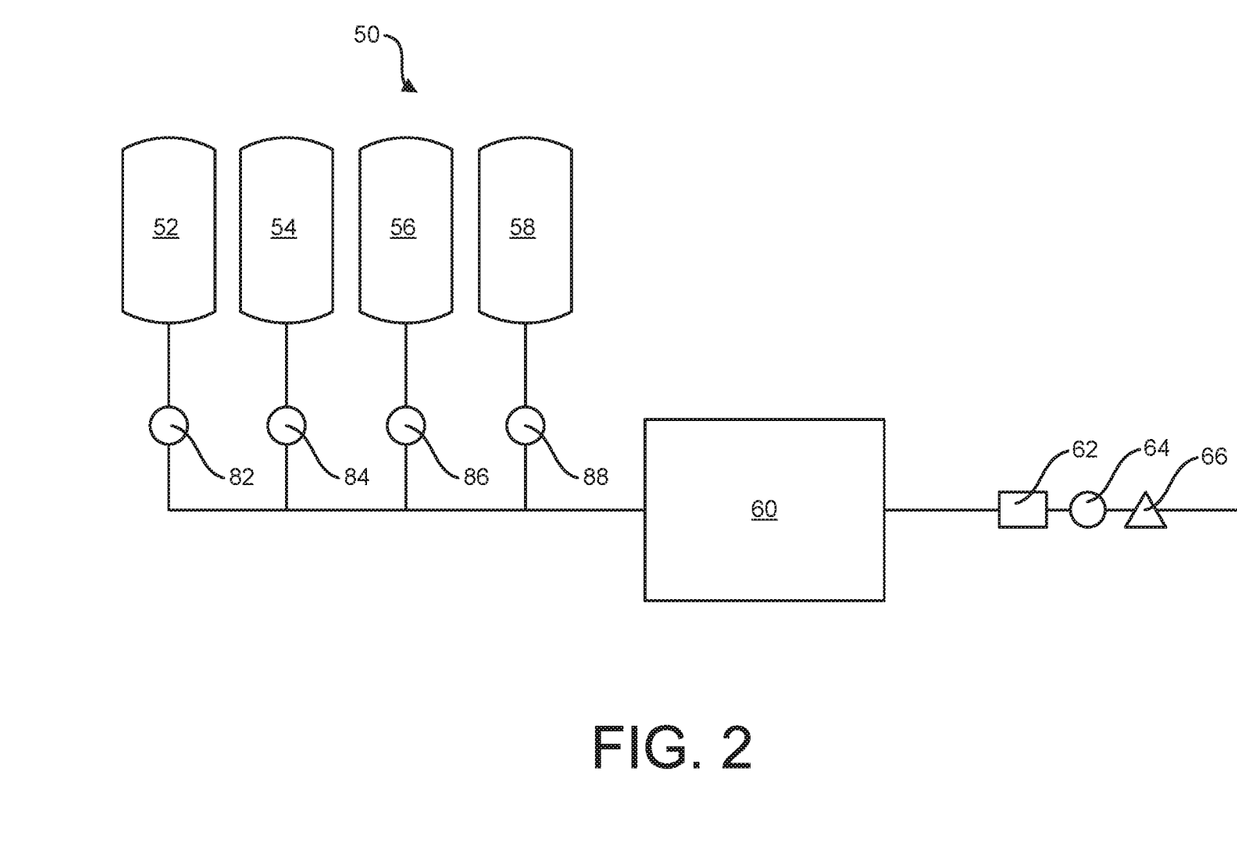
FIG. 2 is a schematic diagram of one embodiment of a buffer formulation system made in accordance with the present disclosure.

In one embodiment, the controller 70 can also be used to monitor each of the buffer solutions contained in the buffer feed tanks 52, 54, 56 and 58. For instance, as shown in FIGS. 1 and 2, each buffer feed tank 52, 54, 56 and 58 can be in communication with a corresponding refractive index measuring device 82, 84, 86 and 88. If desired, each buffer feed tank 52, 54, 56 and 58 can also be in communication with a conductivity probe and/or pH probe. The conductivity measuring devices 82, 84, 86 and 88 can send measurements and other data to the controller 70. In this way, the controller 70 can more accurately determine the composition of each buffer solution. By knowing with greater accuracy the components of each buffer solution, the controller 70 can better control flow rates and maintain the buffer product within preset parameter ranges. For example, in one embodiment, the controller 70 can receive measurements from the conductivity probe 62, the refractive index measuring device 64, and the pH probe 66 and determine whether the buffer product is within preset ranges. The controller 70 can also receive refractive index measurements of each of the individual buffer solutions from the refractive index measurement devices 82, 84, 86 and 88. If the buffer product is outside of any preset ranges, the controller 70 can then automatically control the flow control devices 72, 74, 76 and 78 based upon the refractive index measurements of the individual buffer solutions in order to make any corrections to the buffer product being formulated. The process and system can occur inline and can be used to formulate many different buffer products for delivering to the different stages of the bioprocess. For instance, different buffer products can be formulated for the bioreactor 10, the first filtering device 42, the chromatography device 44, and/or the second filtering device 46.

The devices, facilities and methods described herein are suitable for culturing any desired cell line including prokaryotic and/or eukaryotic cell lines. Further, in embodiments, the devices, facilities and methods are suitable for culturing suspension cells or anchorage-dependent (adherent) cells and are suitable for production operations configured for production of pharmaceutical and biopharmaceutical products—such as polypeptide products, nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesised by the eukaryotic cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2011/0280797; 2009/0305626; and U.S. Pat. Nos. 8,298,054; 7,629,167; and 5,656,491, which are hereby incorporated by reference in their entirety, describe example facilities, equipment, and/or systems that may be suitable.

In embodiments, the cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, YO, C127, L cell, COS, e.g., COS1 and COS7, QC1-3,HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBv13.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cells are for cell therapy.

In one embodiment, the cells may include T cells, or immune cells. For instance, the cells can include B cells, natural killer cells, dendritic cells, tumor infiltrating lymphocytes, monocytes, megakaryocytes, or the like.

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57Bl/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, North Carolina, USA 27709.

In one embodiment, the eukaryotic cell is a lower eukaryotic cell such as e.g. a yeast cell (e.g., *Pichia* genus (e.g. *Pichia pastoris, Pichia methanolica, Pichia kluyveri*, and *Pichia angusta*), *Komagataella* genus (e.g. *Komagataella pastoris, Komagataella pseudopastoris* or *Komagataella phaffii*), *Saccharomyces* genus (e.g. *Saccharomyces cerevisae, cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii,*), the *Geotrichum* genus (e.g. *Geotrichum fermentans*), *Hansenula polymorpha, Yarrowia lipolytica*, or *Schizosaccharomyces pombe*,. Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger, A. fumigatus, A. orzyae, A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora, Bacillariophyceae, Dunaliella, Chlorella, Chlamydomonas, Cyanophyta* (cyanobacteria), *Nannochloropsis, Spirulina*, or *Ochromonas*), or a plant cell (e.g., cells from monocotyledonous plants (e.g., maize, rice, wheat, or Setaria), or from a dicotyledonous plants (e.g., cassava, potato, soybean, tomato, tobacco, alfalfa, Physcomitrella patens or Arabidopsis).

In one embodiment, the cell is a bacterial or prokaryotic cell.

In embodiments, the prokaryotic cell is a Gram-positive cells such as *Bacillus, Streptomyces Streptococcus, Staphylococcus* or *Lactobacillus. Bacillus* that can be used is, e.g. the *B. subtilis, B. amyloliquefaciens, B. licheniformis, B. natto,* or *B. megaterium.* In embodiments, the cell is *B. subtilis,* such as *B. subtilis* 3NA and *B.subtilis* 168. *Bacillus* is obtainable from, e.g., the *Bacillus* Genetic Stock Center, Biological Sciences 556, 484 West 12th Avenue, Columbus OH 43210-1214.

In one embodiment, the prokaryotic cell is a Gram-negative cell, such as *Salmonella* spp. or *Escherichia coli,* such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

In embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

In embodiments, the protein is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-nl, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin,Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin detemir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CIVIL vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, S pneumoniae pediatric vaccine, malaria vaccine, Neisseria meningitidis Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA), infliximab (REMICADE™), rituximab (RITUXAN™/MAB THERA™) etanercept (ENBREL™), bevacizumab (AVASTIN™), trastuzumab (HERCEPTIN™), pegrilgrastim (NEULASTA™), or any other suitable polypeptide including biosimilars and biobetters.

Other suitable polypeptides are those listed below and in Table 1 of US2016/0097074 :

TABLE I

| Protein Product | Reference Listed Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| Interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ® g/Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/ Norditropin Nordiflex ® |
| Mitoxantrone | Novantrone ® |
| insulin; zinc suspension; | Novolin L ® |

TABLE I-continued

| Protein Product | Reference Listed Drug |
|---|---|
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated *Bacillus* Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |
| interferon alfa-2$^a$ | Roferon-A ® |
| Somatropin | Saizen ® |
| synthetic porcine secretin | SecreFlo ™ |
| Basiliximab | Simulect ® |
| Eculizumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In embodiments, the polypeptide is a hormone, blood clotting/coagulation factor, cytokine/growth factor, antibody molelcule, fusion protein, protein vaccine, or peptide as shown in Table 2.

TABLE 2

| Exemplary Products | | |
|---|---|---|
| Therapeutic Product type | Product | Trade Name |
| Hormone | Erythropoietin, Epoein-α Darbepoetin-α | Epogen, Procrit Aranesp |
| | Growth hormone (GH), somatotropin | Genotropin, Humatrope, Norditropin, NovIVitropin, Nutropin, Omnitrope, Protropin, Siazen, Serostim, Valtropin |
| | Human follicle-stimulating hormone (FSH) | Gonal-F, Follistim |
| | Human chorionic gonadotropin | Ovidrel Luveris |
| | Lutropin-α | GlcaGen |
| | Glucagon | Geref |
| | Growth hormone releasing hormone (GHRH) | ChiRhoStim (human peptide), SecreFlo (porcine peptide) |
| | Secretin | Thyrogen |
| | Thyroid stimulating hormone (TSH), thyrotropin | |
| Blood Clotting/ Coagulation Factors | Factor VIIa | NovoSeven |
| | Factor VIII | Bioclate, Helixate, Kogenate, Recombinate, ReFacto |
| | Factor IX | Benefix |
| | Antithrombin III (AT-III) | Thrombate III |
| | Protein C concentrate | Ceprotin |
| Cytokine/ Growth factor | Type I alpha-interferon | Infergen |
| | Interferon-αn3 (IFNαn3) | Alferon N |
| | Interferon-β1a (rIFN-β) | Avonex, Rebif Betaseron |
| | Interferon-β1b (rIFN-β) | Actimmune Proleukin |
| | Interferon-β1b (IFNβ) | Kepivance |
| | Aldesleukin (interleukin 2(IL2), epidermal theymocyte activating factor; ETAF | Regranex Anril, Kineret Avastin Erbitux |
| | Palifermin (keratinocyte growth factor; KGF) | Vectibix Campath |
| | Becaplemin (platelet-derived growth factor; PDGF) | Rituxan Herceptin Orencia |
| | Anakinra (recombinant IL1 antagonist) | Humira Enbrel |
| Antibody molecules | Bevacizumab (VEGFA mAb) | Remicade Amevive |
| | Cetuximab (EGFR mAb) | Raptiva |
| | Panitumumab (EGFR mAb) | Tysabri Soliris |
| | Alemtuzumab (CD52 mAb) | Orthoclone, OKT3 |
| | Rituximab (CD20 chimeric Ab) | |
| | Trastuzumab (HER2/Neu mAb) | |
| | Abatacept (CTLA Ab/Fc fusion) | |
| | Adalimumab (TNFα mAb) | |
| | Etanercept (TNF receptor/Fc fusion) | |
| | Infliximab (TNFα chimeric mAb) | |
| | Alefacept (CD2 fusion protein) | |
| | Efalizumab (CD11a mAb) | |
| | Natalizumab (integrin α4 subunit mAb) | |
| | Eculizumab (C5mAb) | |
| | Muromonab-CD3 | |
| Other: Fusion proteins/ Protein vaccines/ Peptides | Insulin | Humulin, Novolin |
| | Hepatitis B surface antigen (HBsAg) | Engerix, Recombivax HB |
| | HPV vaccine | Gardasil LYMErix |
| | OspA | Rhophylac |
| | Anti-Rhesus(Rh) immunoglobulin G | Fuzeon QMONOS |
| | Enfuvirtide | |
| | Spider silk, e.g., fibrion | |

In embodiments, the protein is multispecific protein, e.g., a bispecific antibody as shown in Table 3.

TABLE 3

Bispecific Formats

| Name (other names, sponsoring organizations) | BsAb format | Targets | Proposed mechanisms of action | Development stages | Diseases (or healthy volunteers) |
|---|---|---|---|---|---|
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | T and Ab | CD3, CD19 | Retargeting of T cells to tumor | Phase I | NHL and ALL |
| AFM12 (Affimed Therapeutics) | T and Ab | CD19, CD16 | Retargeting of NK cells to tumor cells | | |
| AFM13 (Affimed Therapeutics) | T and Ab | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, | Nanobody | IL-6R, HSA | Blockade of proinflammatory | Phase I/II | Rheumatoid arthritis |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| Ablynx; | | | cytokine, binds to HSA to increase half-life | | |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A process for formulating buffer products for feeding to a bioprocess comprising:
   combining multiple buffer solutions to form a final buffer product, the multiple buffer solutions including at least a first buffer solution and a second buffer solution;
   measuring a conductivity of the final buffer product;
   measuring a refractive index of the final buffer product;
   comparing the measured conductivity to a preset conductivity range and comparing the measured refractive index to a preset refractive index range; and
   selectively adjusting a flow rate of the first buffer solution in relation to a flow rate of the second buffer solution in order to maintain the conductivity and the refractive index of the final buffer product within the preset ranges.

2. A process as defined in claim 1, wherein the process is a continuous process and wherein the multiple buffer solutions are combined inline to form the final buffer product.

3. A process as defined in claim 1, further comprising the step of measuring the refractive index of each buffer solution as the buffer solution is being combined with the other buffer solutions to form the final buffer product.

4. A process as defined in claim 1, wherein at least certain of the buffer solutions contain a concentrated buffer component that becomes diluted in the final buffer product.

5. A process as defined in claim 1, wherein the measured conductivity and refractive index of the final buffer product are fed to a controller and wherein the controller selectively increases or decreases flow of one or more buffer solutions in order to maintain the refractive index and the conductivity within the preset ranges.

6. A process as defined in claim 1, wherein at least three buffer solutions are combined to form the final buffer product.

7. A process as defined in claim 1, wherein at least four buffer solutions are combined to form the final buffer product.

8. A process as defined in claim 1, wherein the first buffer solution and the second buffer solution include at least one common cation or anion.

9. A process as defined in claim 8, wherein the first buffer solution and the second buffer solution contain at least one buffer component, the buffer component comprising sodium phosphate, sodium acetate, or sodium chloride.

10. A process as defined in claim 1, wherein the refractive index measurement is compared with a measured temperature of the final buffer product in determining whether the measured refractive index is within the preset limits.

11. A process as defined in claim 1, wherein the final buffer product has a refractive index set point and wherein the preset refractive index range is within 10% of the refractive index set point.

12. A process as defined in claim 1, wherein the final buffer product is fed to a cell culture containing mammalian cells.

13. A process as defined in claim 1, wherein the final buffer product is fed to a chromatography process.

14. A process as defined in claim 1, wherein the final buffer product is fed to a filtration process.

15. A process as defined in claim 14, wherein the filtration process comprises an ultrafiltration process, a diafiltration process, or an ultrafiltration/diafiltration process.

16. A bioprocess system comprising:
   a bioreactor defining a hollow interior for receiving a cell culture, the bioreactor including a plurality of ports for feeding and/or removing materials from the hollow interior;
   a nutrient media feed for feeding a nutrient media to the hollow interior of the bioreactor, the nutrient media feed being in fluid communication with at least one of the ports on the bioreactor;
   a buffer feed for feeding a final buffer product to the hollow interior of the bioreactor, or to a downstream process in communication with the bioreactor;
   a plurality of buffer solution feeds that are each in communication with the buffer feed, each of the plurality of buffer solution feeds being in communication with a control device for controlling flow of a respective buffer solution into the buffer feed for formulating a final buffer product;
   a conductivity probe for measuring a conductivity of the final buffer product;
   a refractive index measurement device for measuring a refractive index of the final buffer product; and
   a controller in communication with the conductivity probe and the refractive index measuring device, the controller being configured to compare conductivity measurements and refractive index measurements with a preset conductivity range and a preset refractive index range respectively, the controller, based on the measured conductivity and refractive index, being configured to control a flow rate of the buffer solutions for selectively increasing or decreasing flow of a buffer solution into the buffer feed in order to maintain the final buffer product within the preset conductivity range and the preset refractive index range.

17. A system as defined in claim 16, wherein the system includes at least three buffer solution feeds that are in fluid communication with the buffer feed.

18. A system as defined in claim 16, further comprising refractive index measuring devices located to measure a refractive index of each buffer solution leaving each buffer solution feed and wherein the controller receives refractive index measurements taken by the refractive index measuring devices in communication with each of the buffer solution feeds.

19. A system as defined in claim 16, wherein the system further includes a temperature sensor for measuring a temperature of the final buffer product, and wherein the temperature measurements taken by the temperature sensor are feed to the controller and wherein the controller is configured to compare the measured temperature with the measured refractive index of the final buffer product for determining whether the final buffer product is within the preset refractive index range.

20. A system as defined in claim 16, wherein the controller is programmed with a refractive index set point and wherein the preset refractive index range is within 10% of the refractive index set point.

21. A system as defined in claim 16, wherein the buffer solutions each contain at least one of tricine, bicine, a sulfonic acid, sodium cacodylate, sodium acetate, sodium phosphate, sodium chloride, an acetic acid, glycinamide, or acetamidoglycine.

* * * * *